(12) United States Patent
Novak et al.

(10) Patent No.: US 11,986,541 B2
(45) Date of Patent: *May 21, 2024

(54) METHOD OF PREVENTING THE DEVELOPMENT OF MELANOMA

(71) Applicant: Vector Vitale IP LLC, North Miami Beach, FL (US)

(72) Inventors: Peter Novak, Sunny Isles Beach, FL (US); Max Temnik, Miami, FL (US); Oleksandr Balakin, Dnepropetrovsk (UA)

(73) Assignee: Vector Vitale IP LLC, North Miami Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/232,013

(22) Filed: Aug. 9, 2023

(65) Prior Publication Data

US 2023/0381347 A1 Nov. 30, 2023

Related U.S. Application Data

(63) Continuation of application No. 17/969,297, filed on Oct. 19, 2022, now Pat. No. 11,730,835, which is a continuation of application No. 16/692,584, filed on Nov. 22, 2019, now Pat. No. 11,484,610.

(51) Int. Cl.
*A61K 51/04* (2006.01)
*A61K 31/164* (2006.01)
*A61K 33/30* (2006.01)
*A61P 35/00* (2006.01)

(52) U.S. Cl.
CPC ........ *A61K 51/0476* (2013.01); *A61K 31/164* (2013.01); *A61K 33/30* (2013.01); *A61P 35/00* (2018.01)

(58) Field of Classification Search
CPC ........... A61K 51/04; A61P 35/00; A61P 35/02
See application file for complete search history.

(56) References Cited

U.S. PATENT DOCUMENTS

| | | |
|---|---|---|
| 4,195,094 A | 3/1980 | Fox, Jr. |
| 8,512,676 B1 | 8/2013 | Eghbalnia et al. |
| 8,753,889 B1 | 6/2014 | Roeder |
| 9,861,659 B2 | 1/2018 | Novak et al. |
| 10,183,041 B2 | 1/2019 | Novak et al. |
| 10,226,484 B2 | 3/2019 | Novak et al. |
| 2003/0068351 A1 | 4/2003 | Roig |
| 2003/0118713 A1 | 6/2003 | Bjorkstrom et al. |
| 2004/0013732 A1 | 1/2004 | Farber et al. |
| 2004/0086453 A1 | 5/2004 | Howes |
| 2007/0207191 A1 | 9/2007 | Kanzer et al. |
| 2011/0117210 A1* | 5/2011 | Ugolkov .............. A61K 31/315 424/643 |
| 2015/0056297 A1 | 2/2015 | Liu |
| 2016/0151415 A1* | 6/2016 | Novak ................. A61K 33/00 424/722 |
| 2016/0153957 A1 | 6/2016 | Novak et al. |
| 2017/0368209 A1 | 12/2017 | Alqathami |
| 2018/0055879 A1* | 3/2018 | Novak ................... A61K 33/06 |
| 2018/0296596 A1 | 10/2018 | Novak et al. |
| 2019/0105345 A1 | 4/2019 | Novak et al. |

FOREIGN PATENT DOCUMENTS

| | | |
|---|---|---|
| WO | 0182871 A2 | 11/2001 |
| WO | 2006072054 A1 | 7/2006 |

OTHER PUBLICATIONS

Uspenskaya et al.,, "Kinetics of Active Pharmaceutical Ingredient Solubility in Water with Different Hydrogen Isotopic Content," Research Paper, Mar.-Apr. 2018, Indian Journal of Pharmaceutical Sciences, pp. 318-324.
Office Action received in U.S. Appl. No. 16/722,249 dated Aug. 31, 2023, pp. 1-18.
Albarede, "Medical applications of the Cu, Zn, and S Isotope effects," Metallomics, Jul. 25, 2016, pp. 1056-1070.
CRC Handbook of Chemistry and Physics (49th ed. 1968), pp. 1-3.
IRMM, Institute for Reference Materials and Measurements: Certificate (Zinc isotopes), Jul. 2007, pp. 1-2.
Jefferson Lab: "It's Elemental", Zinc isotopes, Science Education, May 2017, pp. 1-3.
U.S. Department of Energy "Products and Services Isotope Catalog" 2014, pp. 1-10.
International Application No. PCT/US19/55770 filed Oct. 11, 2019, not yet published.
U.S. Appl. No. 16/722,167, filed Dec. 20, 2019, not yet published.
U.S. Appl. No. 16/722,225, filed Dec. 20, 2019, not yet published.
U.S. Appl. No. 16/722,249, filed Dec. 20, 2019, not yet published.
U.S. Appl. No. 16/722,295, filed Dec. 20, 2019, not yet published.
International Application No. PCT/US2019/067746, International Search Report and Written Opinion dated Sep. 9, 2020, 14 pages.
Ruz et al., "Nutritional Effects of Zinc on Metabolic Syndrome and Type 2 Diabetes: Mechanisms and Main Findings In Human Studies," Biological Trace Element Research, vol. 188, No. 1, 2019, pp. 177-188.
Ranasinghe et al., "Zinc and 1-11 Diabetes Mellitus: Understanding Molecular Mechanisms and Clinical Implications," Daru Journal of Pharmaceutical Sciences, vol. 23, No. 1, 2015, pp. 1-13.

(Continued)

*Primary Examiner* — Michael G. Hartley
*Assistant Examiner* — Jagadishwar R Samala
(74) *Attorney, Agent, or Firm* — Liang & Hennessey LLP; Stanley D. Liang

(57) ABSTRACT

A method for treating melanoma or preventing the development of melanoma comprising administration of a composition comprising $^{64}Zn_e(Asp)_2$ in a therapeutically effective amount. Such administration may be via injection such as intratumoral and/or intravenous injection and may be once a day or more than once a day. A composition for the treatment of or prevention of melanoma comprising $^{64}Zn_e(Asp)_2$ in a therapeutically effective amount. The composition may be a liquid suitable for injection.

5 Claims, 5 Drawing Sheets

(56) References Cited

OTHER PUBLICATIONS

De Carvalho et al., "Zinc's Role in the Glycemic Control of Patients with Type 2 Diabetes: a Systematic Review," Biometals, Kluwer Academic Publishers, vol. 30, No. 2, 2017, pp. 151-162.

Krebs et al.; "The Use of Stable Isotope Techniques to Assess Zinc Metabolism," 1995, ELSEVIER; Nutrientional Biochemistry, vol. 6, pp. 292-301. (Year: 1995).

Mohommad et al.; "Zinc and Liver Disease," Nutrition in Clinical Practice: Official Publication f the American Society for Parenteral and Enteral Nutrition, vol. 27, No. 1, p. 8-20 (Year: 2012).

Office Action received in U.S. Appl. No. 16/722,249 dated Mar. 31, 2021.

International Application No. PCT/US19/62803, International Search Report and Written Opinion dated Jul. 22, 2020, 9 pages.

Himoto et al.; "Associations between Zinc Deficiency and Metabolic Abnormalities in Patients with Chronic Liver Disease," (Jan. 14, 2018), MDPI; Nutrients, vol. 10, No. 88, pp. 1-17. (Year: 2018).

Pearlman et al.; "State of the art: treatment of nonalcoholic steatohepatits," (2014), Lipponcott Williams & Wilkins; Current Opinion in Gastroenterology, vol. 30, No. 3, pp. 223-237. (Year: 2014).

PubChem entry for "Zinc: Other Experimental Properties", retrieved from: <pubchem.ncbi.nlm.nih.gov/compound/23994#section=Other-Experimental-Properties&fullscreen=true> on Jun. 8, 2020, p. 1. (Year: 2020).

Office Action received in U.S. Appl. No. 16/722,249 dated Jun. 26, 2020.

Jayawardena et al., "Effects of Zinc Supplementation on Diabetes Mellitus: A Systematic Review and Meta-Analysis," Diabetology & Metabolic Syndrome, 2012, 4:13, pp. 1-11.

Anyakudo et al., "Dietary Zinc Supplementation in Diabetic Rats: Beneficial Impacts on Glycemic Control and Pancreatic Islet B-cells Regeneration," EC Nutrition, 2017, pp. 224-232.

Office Action received in U.S. Appl. No. 16/722,295 dated May 20, 2020.

Nyenwe et al., "Management of Type 2 Diabetes; Evolving Strategies for the Treatment of Patients with Type 2 Diabetes," Metabolism, Jan. 2011, vol. 60 No. 1, pp. 1-43.

Office Action received in U.S. Appl. No. 16/722,225 dated May 12, 2020.

Borovansky et al., "Cytotoxicity of Zinc in Vitro," Chem-Biol, 1989, pp. 279-291.

Floersheim et al., "Radiation-Induced Lymphoid Tumors and Radiation Lethality are Inhibited by Combined Treatment with Small Doses of Zinc Aspartate and WR 2721," Int. J. Cancer, 52, 1992, pp. 604-608.

JPO, Japanese Application No. 2022-529820, Office Action dated Jun. 20, 2023, pp. 1-3.

* cited by examiner

METHOD OF PREVENTING THE DEVELOPMENT OF MELANOMA

TECHNICAL FIELD

This disclosure relates to oncology, pharmacology and veterinary medicine and relates specifically to treating or preventing malignant skin diseases such as melanoma.

BACKGROUND

Melanoma is a malignant tumor that develops from melanocytes (pigment-containing cells that produce melanin), which are predominantly located in the basal layer of the skin's epidermis and the middle layer of the eye (Hurst E A et al., *Archives of Dermatology Research*, 2003, 139: 1067-1073). This type of pathology accounts for 10 percent of all malignant skin lesions. Its annual incidence rate is 5%. Starting from the 1940s, the incidence of melanoma has doubled every year. Melanoma is the sixth most common cancer among men and the seventh most common cancer in women. The average incidence rates for skin melanoma vary from 3-5 cases per 100,000 people per year in the Mediterranean countries to 12-20 cases per 100 thousand people per year in the Nordic countries and continue to grow. The death rate is 2-3 cases per 100 thousand people every year with slight changes depending on the geographical location, and has remained relatively stable over the past decade. An increased exposure to ultraviolet radiation of a genetically predisposed population, at least in part, results in a steady increase in melanoma incidence over the past decades (Oncology Clinical Practice Guidelines of the European Society for Medical Oncology (ESMO), 2010, p. 294-300). Malignant melanoma is responsible for 60-80% of deaths from skin cancers and its five-year survival rate is 14%. In the United States, 2% of the population was diagnosed with this type of skin cancer, which is a cause of approximately 10,000 deaths every year. At the same time melanoma is a tumor with an extremely high potential of systemic metastases.

Yet, possibilities for treating or preventing melanoma are limited.

SUMMARY

In one aspect, a method is provided of preventing the development of melanoma comprising intratumoral and/or intravenous administration to a subject of $^{64}Zn_e(Asp)_2$, containing 2 molecules of aspartic acid for each molecule of zinc, at a therapeutically effective dose. The non-$^{64}Zn$-enriched form is known as zinc di-aspartate and has a molecular formula $Zn(C_4H_6NO_4)_2$. In certain embodiments, the aspartate of $^{64}Zn_e(Asp)_2$ is enriched for the L-enantiomer. In further embodiments, it is at least 90% L-enantiomer, at least 95% L-enantiomer, or least 98% L-enantiomer.

In another aspect, a method is provided of preventing melanoma metastasis comprising intratumoral and/or intravenous administration to a subject of $^{64}Zn_e(Asp)_2$, containing 2 molecules of aspartic acid for each molecule of zinc, at a therapeutically effective dose.

In yet another aspect, a composition is provided for use in preventing the development of melanoma and/or in preventing melanoma metastasis comprising $^{64}Zn_e(Asp)_2$ in a therapeutically effective amount and at least one carrier or excipient.

In each of the above aspects, in certain embodiments, the $^{64}Zn$-enriched zinc of the $^{64}Zn_e(Asp)_2$ is at least 80% $^{64}Zn$, at least 85% $^{64}Zn$, at least 90% $^{64}Zn$, at least 95% $^{64}Zn$, or at least 99% $^{64}Zn$. Examples of suitable levels of $^{64}Zn$ enrichment include any specific value within the recited ranges, such as 80%, 85%, 90%, 95%, 99%, and 99.8% $^{64}Zn$. As used herein, unless otherwise indicated, X % $^{64}Zn$ means that, out of 100 zinc atoms, X is $^{64}Zn$. For example, in zinc that is 95% $^{64}Zn$, 95% of the atoms are $^{64}Zn$. Unless otherwise indicated, the term "$^{64}Zn_e$" is used herein as shorthand for "$^{64}Zn$-enriched zinc".

BRIEF DESCRIPTION OF THE DRAWINGS

FIG. 4A—control, FIG. 4B-intravenous injection of $^{64}Zn_e(Asp)_2$ 24 hours after transplantation of tumor cells, FIG. 4C-intravenous administration of $^{64}Zn_e(Asp)_2$ 45 minutes after transplantation of tumor cells.

DETAILED DESCRIPTION

Figure 1:
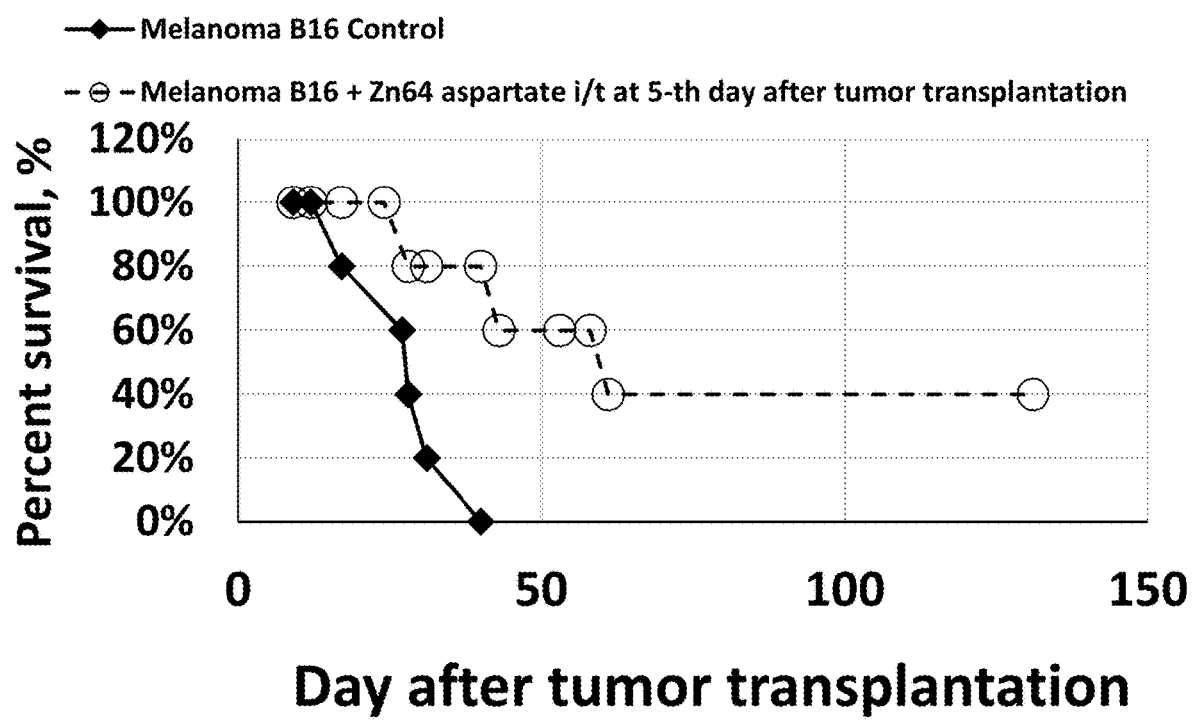
FIG. 1 shows survival data for experimental animals (% vs. control) that were given intratumoral ("i/t") injections of $^{64}Zn_e(Asp)_2$ comprising 2 molecules of aspartic acid/atom of zinc (written in shorthand herein as "$^{64}Zn_e(Asp)_2$", unless otherwise indicated) at day 5 after transplantation of B16 melanoma cells into mice. Data on survival in the group treated with $^{64}Zn_e(Asp)_2$ (intra-tumor administration of $^{64}Zn_e(Asp)_2$ at 5th day after tumor transplantation) are compared with those in the control group.

As used herein, the word "a" or "plurality" before a noun represents one or more of the particular noun.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

The term "treating" as used herein with respect to a medical condition such as melanoma means diminishing the severity and/or consequences of the condition, slowing the progression of the condition, preventing the spread of the condition in a patient who has the condition, preventing metastasis of the condition, at least substantially, and/or curing the condition.

The term "preventing" as used herein with respect to a medical condition such as melanoma means preventing the development of the condition, at least substantially, diminishing the severity and/or consequences of the condition, slowing the progression of the condition, preventing the spread of the condition in a patient who has the condition, and/or preventing metastasis of the condition, at least substantially.

"Effective amount," "prophylactically effective amount," or "therapeutically effective amount" refers to an amount of an agent or composition that provides a beneficial effect or favorable result to a subject, or alternatively, an amount of an agent or composition that exhibits the desired in vivo or in vitro activity. "Effective amount," "prophylactically effective amount," or "therapeutically effective amount" refers to an amount of an agent or composition that provides the desired biological, therapeutic, and/or prophylactic result. That result can be reduction, amelioration, palliation, lessening, delaying, prevention, and/or alleviation of one or more of the signs, symptoms, or causes of a disease, disorder or condition in a patient/subject, or any other desired alteration of a biological system. With regards to cell proliferation disorders, a favorable result includes reducing impacts or severity of symptoms associated with a disease or disorder and/or increasing life expectancy compared to that in the absence of treatment. An effective amount can be administered in one or more administrations. The relationship between the dose levels in animals and humans (based on milligrams per square meter of body surface area) is described, for example, in Freireich et al., (1966) Cancer Chemother Rep 50: 219.

For any composition, an effective amount can be first estimated either in accordance with cell culture assays or using animal models, typically mice, rats, guinea pigs, rabbits, dogs or pigs. An animal model may be used to determine an appropriate concentration range and route of administration. Such information can then be used to determine appropriate doses and routes of administration for humans. When calculating a human equivalent dose, it is recommended to use a conversion table given in the Guidance for Industry and the Reviewers document (2002, US Food and Drug Administration, Rockville, MD, USA). An effective daily dose is generally 0.01 mg/kg patient weight to 2000 mg/kg patient weight of an active agent, preferably 0.05 mg/kg patient weight to 500 mg/kg patient weight of an active agent. An exact effective dose will depend on the severity of the disease, patient's general state of health, age, body weight and sex, nutrition, time and frequency of administration, combination(s) of medicines, response sensitivity and tolerance/response to administration and other factors that will be taken into account by a person skilled in the art when determining the dosage and route of administration for a particular patient based on his/her knowledge of the art. Such dose may be determined by conducting routine experiments and at the physician's discretion. Effective doses will also vary depending on the possibility of their combined use with other therapeutic procedures, such as the use of other agents.

As used herein, a "patient" and a "subject" are interchangeable terms and may refer to a human patient/subject, a dog, a cat, a non-human primate, etc.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Melanoma

Melanoma is a malignant tumor that develops from melanocytes (pigment-containing cells that produce melanin), which are predominantly located in the basal layer of the skin's epidermis and the middle layer of the eye (Hurst E A et al., *Archives of Dermatology Research*, 2003, 139: 1067-1073). This type of pathology accounts for 10 percent of all malignant skin lesions. Its annual incidence rate is 5%. Starting from the 1940s, the incidence of melanoma has doubled every year. Melanoma is the sixth most common cancer among men and the seventh most common cancer in women. The average incidence rates for skin melanoma vary from 3-5 cases per 100,000 people per year in the Mediterranean countries to 12-20 cases per 100 thousand people per year in the Nordic countries and continue to grow. The death rate is 2-3 cases per 100 thousand people every year with slight changes depending on the geographical location, and has remained relatively stable over the past decade. An increased exposure to ultraviolet radiation of a genetically predisposed population, at least in part, results in a steady increase in melanoma incidence over the past decades (Oncology Clinical Practice Guidelines of the European Society for Medical Oncology (ESMO), 2010, p. 294-300). Malignant melanoma is responsible for 60-80% of deaths from skin cancers and its five-year survival rate is 14%. In the United States, 2% of the population was diagnosed with this type of skin cancer, which is a cause of approximately 10,000 deaths every year. At the same time melanoma is a tumor with an extremely high potential of systemic metastases.

Primary melanoma is resistant to chemotherapy and radiation therapy. The main method of treatment of patients with primary melanoma is surgical removal of the tumor and some normal tissue around it. The amount of tissue removed with surgical excision depends on the tumor thickness (Breslow thickness) and the depth of the tumor invasion. However, surgical treatment of melanoma has a number of significant disadvantages associated with prolonged wound healing and occurrence of implantation metastases within 2 years of the surgery. This method of treatment is used only at early stages of the disease (stage 1-2). At the advanced stages, radiation therapy, chemotherapy, and immunotherapy are additionally used.

Antitumor activity is exhibited by various compounds, such as alkylating compounds, antimetabolites, antibiotics, substances of plant or animal origin, hormonal preparations, and enzymes, which differ in their mechanism of action and chemical structure. However, these chemotherapeutic drugs produce severe adverse effects on normal tissues or organs and thus limiting their usefulness.

Possibilities for treating melanoma are limited. Recently, a number of works have demonstrated that an isotopic composition of tissues and organs may serve as a diagnostic marker. In particular, a study of Cu and Zn isotope ratios in blood showed promising correlations between isotopic values and age, gender and pathologies. For example, determination of copper isotope ratio in blood serum is a new approach for the diagnosis and prognosis of the development of liver cirrhosis (M. Costas-Rodriguez et al., *Isotopic analysis of Cu in blood serum by multi-collector ICP-mass spectrometry: a new approach for the diagnosis and prognosis of liver cirrhosis*, Metallomics 2015, 7: 491-498). Zinc isotopic composition in breast tissue can help in the diagnosis of breast cancer (F. Lamer et al., *Zinc isotopic compositions of breast cancer tissue*, Metallomics 2015, 7: 112-117). Further, certain patents and patent applications discuss the use of isotopically enriched compositions for therapeutic use. See, e.g., U.S. Pat. Nos. 9,861,659; 10,183, 041, and 10,226,484.

WO2007/140280 suggests using an anti-cancer composition for topical administration comprising a cesium ion source and/or a rubidium ion source as pharmaceutically acceptable salts to be used for melanoma treatment. The feasibility of using this therapy is based on an approach that involves changing the acidic pH of cancer cells to slightly alkaline, whereby the survival of cancer cells is compromised, and the formation of acidic and toxic materials, usually formed in cancer cells, is neutralized and eliminated (Sartori H E. Nutrients and cancer: an introduction to cesium therapy, Pharmacol. Biochem. Behav. 1984; 21, Suppl. 1: 7-10). Thus mass spectrographic and isotope studies have shown that potassium, rubidium and cesium are most effectively absorbed by cancer cells. Glucose can still enter the cell but oxygen cannot; therefore, the cell becomes anaerobic. In the absence of oxygen, fermentation of glucose to lactic acid occurs, and the pH of the cell is reduced to 7 and finally to 6.5. Cesium, rubidium and potassium, which create high pH values, are able to enter the cell in such state and increase its pH value. In this setting, cesium and rubidium ions can change ionic physiology of the cancer cell, including inhibition of the transmembrane movement of potassium. It is assumed that cesium and rubidium efficiently control potassium and bound hydrogen ion ($H^+$) fluxes that affect all acid-dependent cancers and provide site affinity for selective increase in the pH of the tumor microenvironment. In the author's opinion, this provides selective tumor modulation, but the application materials do not contain any information that would confirm the effectiveness of using this composition to treat cancer. In addition, the composition described in this application is for topical administration, which cannot provide high efficacy in treating a patient. Thus the use of the described approach, although targeted on cancer cells, still is not able to provide effective eradication of tumor cells, but rather can only be used as a food supplement in addition to other methods of treatment.

Methods

In one aspect, a method is provided for preventing the development of melanoma. The method effectively suppresses the development of a malignant tumor without surgical intervention and damage to surrounding normal tissues, and additionally exhibits a high anti-metastatic effect. The use of the claimed method makes it possible to achieve effective inhibition of the development of melanoma without producing adverse effects on the body, as is characteristic of chemotherapeutic drugs. The method comprises administering to a subject in need thereof a light isotope of zinc in the form of aspartic acid salt. A pharmaceutical composition is provided to be used in the disclosed method for preventing the development of melanoma, which comprises $^{64}Zn_e(Asp)_2$ in a therapeutically effective amount. The disclosed method has high efficacy in inhibiting the growth of tumor cells, along with low toxic effect.

A method of treating melanoma or preventing the development of melanoma is disclosed. The method comprises intratumoral and/or intravenous administration of a composition that contains $^{64}Zn_e(Asp)_2$ in a therapeutically effective amount. The administration of the composition may be single or multiple. In certain embodiments, the treatment regimen comprises 5 to 10 injections of $^{64}Zn_e(Asp)_2$. In certain embodiments, the aspartate present in $^{64}Zn_e(Asp)_2$ is at least 90% the L-enantiomer, at least 95%, at least 98%, or all L-isomer. In some embodiments, it may be the D-enantiomer and in other embodiments it may be a mixture of the two enantiomers.

A method is provided of treating melanoma or preventing the development of melanoma comprising the administration of a composition comprising a therapeutically effective amount of $^{64}Zn_e(Asp)_2$ to a patient in need thereof. In some embodiments, the composition is an aqueous solution. In some embodiments, the composition is administered intratumorally or intravenously. In some embodiments, the $^{64}Zn_e(Asp)_2$ comprises 2 molecules of aspartic acid. In some embodiments, from 0.2 μg/kg patient weight/day to 2000 mg/kg patient weight/day of $^{64}Zn_e(Asp)_2$ is administered to the patient. In some embodiments, from 0.01 mg/kg/day to 5 mg/kg/day of $^{64}Zn_e(Asp)_2$ is administered to the patient. In some embodiments, wherein from 0.1 mg/kg/day to 1 mg/kg/day of $^{64}Zn_e(Asp)_2$ is administered to the patient. In some embodiments, the composition is administered once a day. In other embodiments, the composition is administered more than once a day. In some embodiments, the composition further comprises deuterium-depleted water as a solvent. In some embodiments, the method of treating/preventing melanoma is a method that prevents, delays, or ameliorates melanoma metastasis.

Enantiomeric purity of the aspartate in $^{64}Zn_e(Asp)_2$ may be determined by methods known in the art, such as, for example, chiral chromatography.

The presence of zinc in the $^{64}Zn_e(Asp)_2$ compound or other zinc-containing compounds may be confirmed by methods known in the art, such as, for example, atomic emission spectroscopy with an inductively coupled plasma. Prior to subjecting the sample to atomic emission spectroscopy with an inductively coupled plasma, the sample may be treated with a mixture of mineral acids in a Teflon autoclave under the action of microwave radiation.

Elemental impurities or impurities of sulfate ion in the $^{64}Zn_e(Asp)_2$ compound or other zinc-containing compounds may be determined by methods known in the art, such as, for example, atomic emission spectroscopy with an inductively coupled plasma. Prior to subjecting the sample to atomic emission spectroscopy with an inductively coupled plasma, the sample may be treated with a mixture of mineral acids in a Teflon autoclave under the action of microwave radiation.

Light isotopes may be purchased. Zn-64 oxide with the necessary degree of enrichment may be purchased from, for example, Oak Ridge National laboratory, Oak Ridge, TN, USA.

In certain embodiments, an effective amount of $^{64}Zn_e$ administered to a subject in need thereof may be from 0.2 μg/kg patient weight/day to 2000 mg/kg patient weight/day. This range of from 0.2 μg/kg/day to 2000 mg/kg/day corresponds to the amount of zinc present in the composition as part of aspartate. In further embodiments, the range of $^{64}Zn_e$ administered is from 0.01 mg/kg/day to 5 mg/kg/day, more preferably 0.1 mg/kg/day to 1 mg/kg/day. Compositions for use in the disclosed methods contain corresponding amounts. For example, a composition for use of a disclosed method contains an amount of $^{64}Zn_e$ such that a single dose of the composition contains from 1 to 100 mg $^{64}Zn_e$ in the form of $^{64}Zn_e(Asp)_2$, such as 1, 5, 10, 20, 30, 40, 50, or 100 mg $^{64}Zn_e$. An exemplary composition is a solution of $^{64}Zn_e(Asp)_2$ that contains 1 mg $^{64}Zn_e$ per ml of solution. In some embodiments, the solvent is deuterium-depleted water. The solution is formulated for oral or parenteral administration, such as administration by injection, such as by intratumoral or intravenous administration. Compositions for injection may be aqueous solutions, such as solutions with a salinity and pH optimized for the route of injection. The solution may contain excipients such as DMSO. The DMSO may be present at a concentration of 1%. Another exemplary composition for used in the disclosed method is a tablet or other solid composition for oral administration that contains 30 mg $^{64}Zn_e$. The composition may also be a liquid for oral administration, such as an aqueous composition, for example, a syrup.

A treatment regimen of the disclosed method can include either intratumoral administration or intravenous administration of a composition for use in a disclosed method, or both routes of administration. When both routes are used in a patient, the same composition may be administered via both routes, or different compositions may be administered. In some embodiments, combined intratumoral and intravenous administration routes are used.

In the Examples, melanoma model systems are used to study the efficacy of a composition comprising $^{64}Zn_e(Asp)_2$ to simulate in vivo a number of processes of tumor dissemination in warm-blooded animals, including operative/surgical intervention in case of a possible spread of tumor cells to remote sites and/or local niches. Postoperative administration of the composition and/or its administration to prevent a possible melanoma metastatic process (and hence tumor progression) provides suppression of the metastatic process and has significant advantages.

Without having an intention to be associated with any scientific theory, the following explanation of the efficacy of $^{64}Zn_e(Asp)_2$ is offered. Cancer tissues are largely enriched with heavy isotopes (such as $Zn^{70}$) and depleted of light isotopes (such as $^{64}Zn_e$) of the basic elements. Substitution of $^{64}Zn_e$ by $^{70}Zn_e$ ($^{70}Zn$-enriched zinc) may result in an isotope-induced change in the chirality of one or more amino acids in the protein structure and, as a result, may affect the conformation of receptors, ligands, and signal molecules. Loss of the structure correctness, depletion and degradation of proteins may lead to disruption in intra- and intercellular homeostasis, and, as a consequence, to various pathologies. The rate of development of the disease and symptom expression may be slow or rapid, depending on the characteristics of pathological chiral amplification of amino acids due to autocatalytic reactions in living cells.

Generally, the reactions of asymmetric autocatalysis have a nonlinear character of the relationship between yield and time. The most dramatic consequences occur when the above changes take place in the p53 protein, known as the "protector of the genome", two-thirds of which consist of zinc fingers. There are five stable isotopes of zinc. In fact, "wrong" conformation of p53 causes failures in stopping the cell cycle, malfunctions of differentiation, apoptosis, metabolism, genomic stability, angiogenesis, DNA repair, aging, and other processes. What is not known is that the very onset of pathological changes is due to chirality induced by isotope substitution, leading to changes in the conformation of proteins. These changes are apparently reversible, and therefore a return to the normal state can be achieved by using light isotopes. With regard to p53, this may be the $^{64}Zn$ isotope.

The disclosed method results in isotopic selective protein modulation, which makes it possible not only to restore damaged negative feedback in the cell communication system by restoring transmitting and receiving receptors and signal molecules but, more importantly, opens a possibility for eliminating mutations in biomolecules by reactivating the normal functions of p53 protein and associated pathways. The mass spectrometric study shown in the Examples provides confirmation.

The present invention is described more fully hereinafter by reference to the following examples, which are presented by way of illustration only and should not to be construed to in any way limit the scope of the present invention.

EXAMPLES

Example 1. In Vivo Study Supporting the Efficacy of the Claimed Method Carried Out in Mouse Models (Intratumoral Administration of $^{64}Zn_e(Asp)_2$)

B16 melanoma cells having the following characteristic were used in the experiment:

Origin: *Mus musculus* skin (C57BL/6 mouse)

Characteristics of tumor growth: short incubation period, rapid growth, absence of spontaneous metastases.

Tumor inoculability is 100%. The minimum dose of cells that causes tumor growth for this melanoma is only 100 to 1000 per subcutaneous injection in the mouse.

An average life expectancy of animals is 21-31 days.

The tumor cell population is heterogeneous and includes both highly pigmented regions and fragments with a low content of melanin.

Karyotype: The number of chromosomes varies from 30 to 80, 2n=40, the modal number is 72 chromosomes (14%), polyploidy is 3%. All cells contain 2 to 8 interchromosomal associations according to Robertsonian translocations.

A characteristic feature of B16 melanoma cells is a very low mRNA expression level of c-myc, c-jun, and c-fos oncogenes and the absence of c-ras, c-abl, c-erb-B2, B-lym, c-sis andc-myb oncogene expression. Another feature inherent in the cells of this melanoma is that they produce in vitro a large amount of the factor exhibiting procoagulant activity.

A study of the phenotypic characteristics of melanoma cells using immunocytochemical analysis has shown that the cells express VE-cadherin, N- and E-cadherins, Twist and Slug transcription factors, P-glycoprotein, ERCC, DAB2, TAP1 and weakly express CD44.

All studies that involved using mice were conducted in compliance with the rules of the European Convention for the Protection of Vertebrate Animals used for Experimental and Other Scientific Purposes [Commission of the European Communities: Council Directive of 18 Dec. 1986 on the Lows, regulating the Application of Principles of Good Laboratory Practice and the Verification of Their Applications for Tests on Chemical Substances (87/18/EEC). The Rules Governing Medicinal Products in the European Community.—1991.—V.1.-P. 145-146].

The animals were selected according to the objectives of the experiment and in conformity with generally accepted requirements for preclinical studies of test products, including biologic drugs showing antitumor activity.

The animals were maintained in accordance with the standards set forth in The Guide for Care and Use of Laboratory Animals (ILAR publication, 1996, National Academy Press, 1996). During the experiment, the animals were kept in plastic cages, had a natural cycle of daytime and nighttime, were given standard diet and had free access to food and water.

Clinical Observations

All the animals in cages were examined daily in order to determine mortality or any signs of deviations in their health status. A thorough examination was performed each time any abnormalities were detected. All deviations were recorded.

Statistical processing of the results was carried out using STATISTISA 6.0 software package designed for analysis in medical and biological statistics using the Student's t-test; differences with a probability of not less than 95% were considered significant (p<0.05).

15 female $C_{57}B1/J6$ mice (5 mice per group) at the age of 10-12 weeks, weighing 18-22 g were used in the experiment.

B16 melanoma cells were cultured in vitro under standard conditions. For transplantation, tumor cells in the exponential phase were removed from the substrate with 0.02% Versene solution and the suspension cellularity and viability was evaluated in the presence of trypan blue in a hemocytometer and the suspension was adjusted to a concentration of $10^7$ cells/ml by dilution with saline solution. Melanoma cells were injected intracutaneously (i.c.) in 0.05 ml of the suspension ($0.5 \times 10^6$ cells/mouse) into the animal's back region. 24 hours before the injection of tumor cells, the wool cover on the back of each mouse was removed with depilation cream.

Grouping. The animals were divided into groups as follows:

Group No. 1: control group, mice injected i.c. with B16 melanoma cells;

Group No. 2: mice injected i.c. with B16 melanoma cells+ intratumoral injections of $^{64}Zn_e(Asp)_2$ at day 5 after the tumor cells were inoculated.

Group No. 3: mice injected i.c. with B16 melanoma cells+ intratumoral injections of $^{64}Zn_e(Asp)_2$ at day 11 after the tumor cells were inoculated The composition to be administered was prepared immediately prior to its administration. $^{64}Zn_e(Asp)_2$ was dissolved in deuterium-depleted water with addition of 1% DMSO. Animals in group No. 2 were injected with the composition comprising $^{64}Zn_e(Asp)_2$ intratumorally and around the area of tumor growth at a dose of 200 µg/mouse in a volume of 20/mouse after the tumor reached 0.5 cm in diameter (at day 5 after i.c. administration of the tumor cells). The following injection of $^{64}Zn_e(Asp)_2$ was given according to the above scheme in the event an experimental animal had a new tumor growth.

Animals in group No. 3 were injected with the composition comprising $^{64}Zn_e(Asp)_2$ intratumorally and around the area of tumor growth at a dose of 300 µg/mouse in a volume of 30 µl/mouse at day 11 after i.c. administration of the tumor cells. The follow-up injection of $^{64}Zn_e(Asp)_2$ was given in the event an experimental animal had a new tumor growth but at a dose 200 µg/mouse in a volume of 20/mouse. 24 hours after the first injection and then a series of injections were given every other day. $^{64}Zn_e(Asp)_2$ was administered intratumorally every other day for 10 days, 5 times in total.

Regarding the 3rd group: group 3 mice received 300 mcg/mouse of $^{64}Zn_e$ in the form of $4Zn_e$ aspartate on the 11th day and 200 mcg/mouse of $4Zn_e$ aspartate on the 13th, 15th, 17th and 19th days after tumor cell injection.

Regarding the 2nd group: group 2 mice received 200 mcg/mouse of $4Zn_e$ aspartate on the 5th day after tumor cell injection and then $4Zn_e$ aspartate was given in the event an experimental animal had a new tumor growth at a dose 200 mcg/ml.

The anti-tumor efficacy of $^{64}Zn_e(Asp)_2$ was evaluated on the basis of the growth dynamics of melanoma tumors estimated based on the changes in tumor volume according to generally accepted rules.

From the time the experimental tumors reached 0.3-0.5 cm in diameter and every 2-3 days thereafter, the size of each tumor node in experimental animals was measured in three orthogonal planes (width×length×height (W×L×H)) and the tumor volume was calculated by use of the following formula for the volume of ellipsoid: $V=4/3 \times \pi abc$; where V is the tumor volume ($mm^3$); a, b, c is the rumor radius (mm): a is the radius along the x axis, b is the radius along the y axis, c is the radius along the z axis.

Statistical data processing: The Student's t-test was used to see whether there is a statistically significant difference between the means of the groups. Calculations were made using STATISTICA 6.0 software package.

Figure 2:
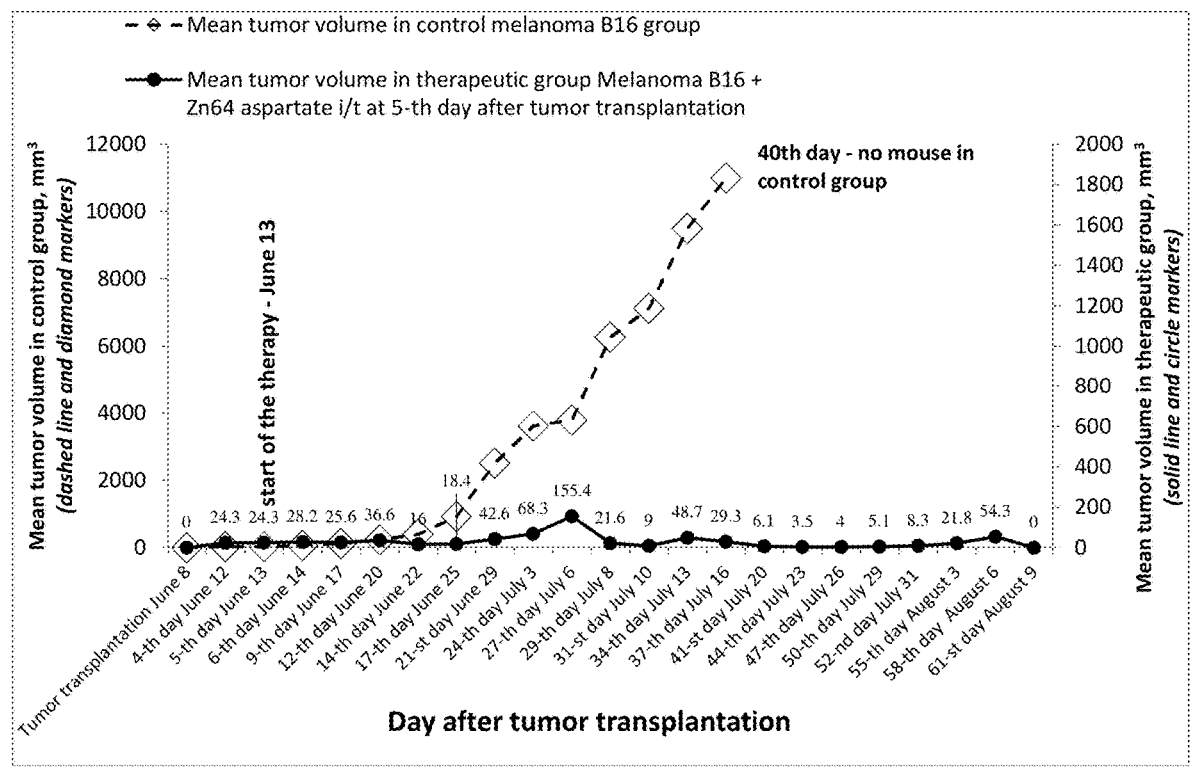
FIG. 2 shows data on the antitumor activity of $^{64}Zn_e(Asp)_2$ in mice (mean tumor volume in mm$^3$) that were given intratumoral injections of $^{64}Zn_e(Asp)_2$ at day 5 after transplantation of B16 melanoma cells compared to the control group.
Figure 3:
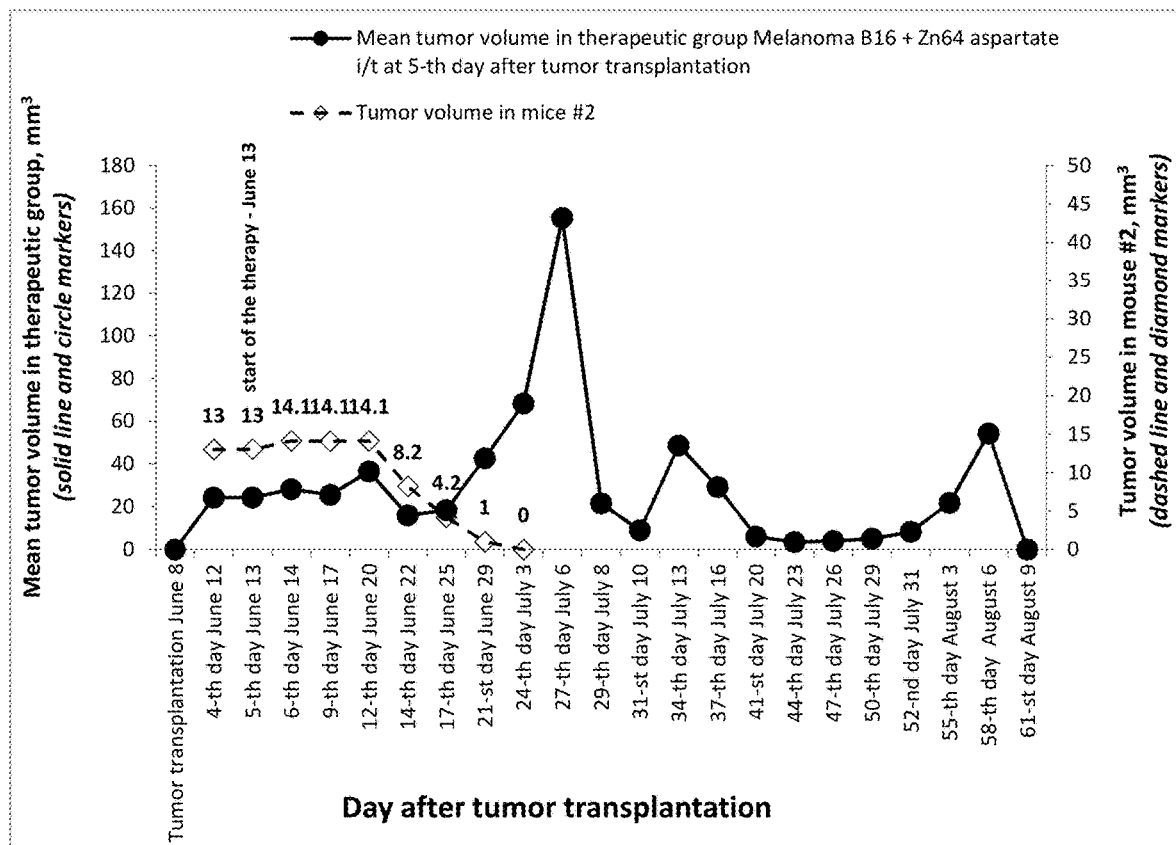
FIG. 3 shows data on the kinetics of B16 melanoma growth in mice (mean tumor volume in mm$^3$) that were given intratumoral injections of $^{64}Zn_e(Asp)_2$ at day 5 after transplantation of B16 melanoma cells compared to the control group.
Figure 4A:
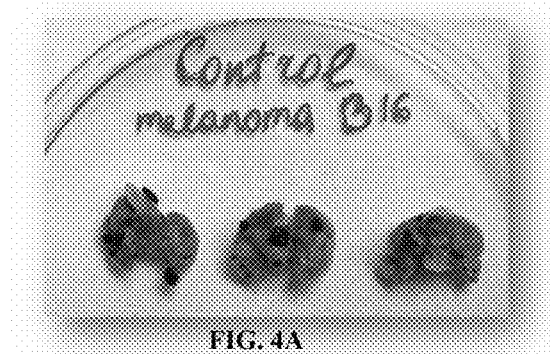
FIGS. 4A-4C shows data on the inhibition of metastatic process in the lungs in C57B1 mice transplanted with B16 melanoma after intravenous administration of $^{64}Zn_e(Asp)_2$ 45 minutes and 24 hours after transplantation of the tumor cells.
Figure 4B:
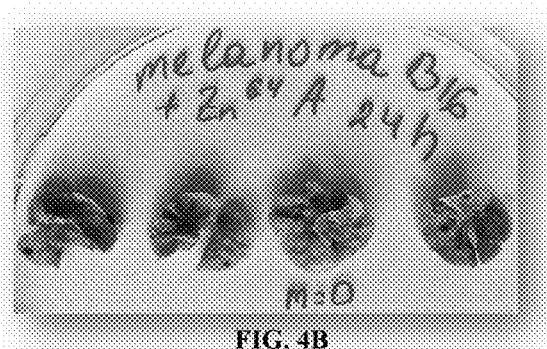
Figure 4C:
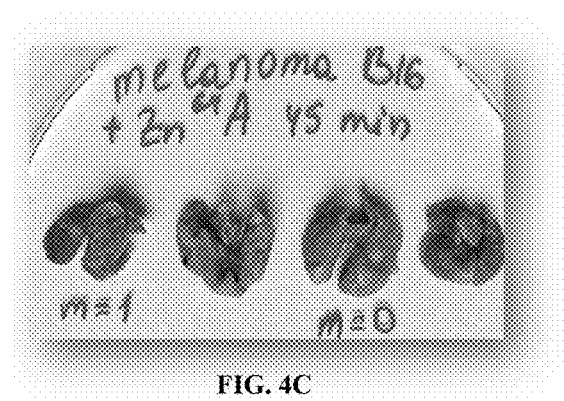

During the study of antitumor activity of the method comprising administration of $^{64}Zn_e(Asp)_2$, results that indicate that intratumoral administration of the composition comprising $^{64}Zn_e(Asp)_2$ suppresses the development of melanoma in mice (see Table 1) were obtained. FIGS. 1-4 show the results of the efficacy of the claimed method in mice. The survival rates of the experimental animals that received intratumoral injections of the composition comprising $^{64}Zn_e(Asp)_2$ were also determined during the experiment (see Table 2).

TABLE 1

Kinetics of B-16 melanoma tumor growth under the effect of $^{64}Zn_e(Asp)_2$

| Experimental group | Day after inoculation of tumor cells |||||||||
|---|---|---|---|---|---|---|---|---|---|
| | 4 | 6 | 9 | 12 | 14 | 17 | 21 | 24 | 27 |
| | Tumor volume, $mm^3$ (M ± m) |||||||||
| B16 melanoma Control | 27.8 ± 3.9 | 69.2 ± 8.6 | 125.4 ± 24.3 | 231 ± 36.8 | 393.3 ± 75.5 | 923 ± 324 | 2504 ± 758 | 3610 ± 731 | 3793.5 ± 495 |
| B16 melanoma + $^{64}Zn_e(Asp)_2$ at day 5 after inoculation of tumor cells | 24.3 ± 3 | 28.2 ± 10$^a$ | 25.6 ± 6.8$^b$ | 36.6 ± 20$^c$ | 16 ± 6$^d$ | 18.4 ± 12$^a$ | 42.6 ± 35$^a$ | 68.3 ± 54$^d$ | 155.4 ± 123$^e$ |

TABLE 1-continued

Kinetics of B-16 melanoma tumor growth under the effect of $^{64}Zn_e(Asp)_2$

| Experimental group | Day after inoculation of tumor cells | | | | | | | | |
|---|---|---|---|---|---|---|---|---|---|
| | 4 | 6 | 9 | 12 | 14 | 17 | 21 | 24 | 27 |
| | Tumor volume, mm³ (M ± m) | | | | | | | | |
| B16 melanoma + $^{64}Zn_e(Asp)_2$ at day 11 after inoculation of tumor cells | 27 ± 4.2 | 63 ± 10 | 119 ± 26 | 260 ± 20 | 184 ± 51 | 250 ± 104 | 375.4 ± 135$^a$ | 881 ± 263.6$^a$ | 2313.5 ± 748.5 |

$^a$p < 0.05, $^b$p < 0.02, $^c$p < 0.01, $^d$p < 0.005, $^e$p < 0.002 vs. control It should also be noted that in group No. 2 (administration of the therapeutic composition at day 5 after inoculation of tumor cells), the growth of melanoma was suppressed by 100% in 2 out of 5 experimental animals after a single intratumoral injection of $^{64}Zn_e(Asp)_2$.-ID-4T

TABLE 2

Survival of laboratory animals (5 animals per group) under the effect of $^{64}Zn_e(Asp)_2$

| Experimental group | Day after inoculation of tumor cells | | | | | | | | | | |
|---|---|---|---|---|---|---|---|---|---|---|---|
| | 4 | 6 | 9 | 12 | 14 | 17 | 21 | 24 | 27 | 28 | 31 |
| | Number of alive mice, % | | | | | | | | | | |
| B16 melanoma Control | 100 | 100 | 100 | 100 | 100 | 80 | 80 | 80 | 60 | 40 | 20 |
| B16 melanoma + $^{64}Zn_e(Asp)_2$ at day 5 after inoculation of tumor cells | 100 | 100 | 100 | 100 | 100 | 100 | 100 | 100 | 100 | 80* | 80 |
| B16 melanoma + $^{64}Zn_e(Asp)_2$ at day 11 after inoculation of tumor cells | 100 | 100 | 100 | 80⁺ | 80 | 80 | 80 | 60* | 60 | 40 | 40 |

*necrosis, ulcer; ⁺the animal died immediately after the injection because of too high dose of the composition.

TABLE 3

Growth kinetics of B16 melanoma during $^{64}Zn_e(Asp)_2$ therapy in group 2 and individual regimens of drug administration

| Group and tumor volume | Day after tumor cell inoculation | | | | | | | | | |
|---|---|---|---|---|---|---|---|---|---|---|
| | 4 day | 5 day | 6 day | 10 day | 12 day | 13 day | 14 day | 17 day | 18 day | 21 day |
| Melanoma B16 Control | 33.5 | | 62 | 94.2 | 199.4 | | 342 | — | | — |
| | 24.4 | | 102 | 211 | 377 | | 692.7 | 1854.6 | | 4456.5 |
| | 14.1 | | 65.4 | 121 | 200.6 | | 282.7 | 864 | | 1466 |
| | 33.5 | | 65.4 | 134 | 201.6 | | 322.5 | 550 | | 2937.4 |
| | 33.5 | | 51 | 67 | 176 | | 326.7 | 424 | | 1157 |
| Melanoma B16 + $^{64}Zn_e(Asp)_2$ IC on day 5 | 14.1 | Tumor+/ 1st injection | 14.1 | 24.4 | 24.4 | — | 14 | 4.2 | — | 0 |
| | 33.5 | Tumor+/ 1st injection | 33.5 | 24.4 | 14 | | 14 | 4.2 | — | 0 |
| | 24.4 | Tumor +/ 1st injection | 14.1 | 14 | 14 | — | 4.2 | 4.2 | | 0 |
| | 25 | Tumor+/ 1st injection | 65.4 | 51 | 116.4 | Tumor+/ 2nd injection | 38.4 | 65.4 | — | 179.6 |
| | 24.4 | Tumor+/ 1st injection | 14.1 | 14 | 14 | Eschar | 9.2 | 14 | Tumor+/ 2nd injection | 33.5 |

TABLE 3-continued

Growth kinetics of B16 melanoma during $^{64}Zn_e(Asp)_2$ therapy in group 2 and individual regimens of drug administration

| Group and tumor volume | Day after tumor cell inoculation | | | | | | | | | |
|---|---|---|---|---|---|---|---|---|---|---|
| | 22 day | 24 day | 25 day | 28 day | 36 day | 39 day | 43 day | 55 day | 58 day | 61 day |
| Melanoma B16 Control | — | 5026.5 | | — | | | | | | |
| | | 2246.2 | | 3298.7 | | | | | | |
| | | 4712.4 | | — | | | | | | |
| | | 2456.7 | | 4288.3 | | | | | | |
| Melanoma B16 + $^{64}Zn_e(Asp)_2$ IC on day 5 | — | 25.4 | Tumor+/ 2nd injection | 33.2 | Tumor+/ 3rd injection | Tumor+ | Tumor+ | $4^{th}$ injection | Tumor+/ Tumor necrosis | Died* |
| | — | 0 | — | 0 Tumor− | Tumor− | Tumor− | Tumor− | Tumor− | Tumor− | Tumor− |
| | — | 0 | — | 0 Tumor− | Tumor− | Tumor− | Tumor− | Tumor− | Tumor− | Tumor− |
| | Tumor+/ 3rd injection | 282.7 | Tumor+/ Tumor necrosis | 641 Died* | — | — | — | — | — | — |
| | — | 33.5 | — | 102.6 Tumor+/ 3rd injection | Tumor+/ 4th injection | Tumor+/ Tumor necrosis | Died* | — | — | — |

Tumor− absence of tumor growth
Tumor+ presence of tumor

As can be seen from the presented data, intratumoral administration of $^{6M}Zn_e(Asp)_2$ on the 5th day after inoculation of tumor cells resulted in a significant reduction in tumor volume (the tumor volume in experimental animals treated with $^{64}Zn_e(Asp)_2$ was 4% of the corresponding figure in the control group). The antitumor effect of $^{6M}Zn_e(Asp)_2$ in the group where drug administered on the 11th day after inoculation of tumor cells first was less pronounced. Statistically significant suppression of tumor growth was observed only on the 21st and 24th days of the experiment. The size of melanoma was reduced by 85% (21st day) and by 75.6% (24th day) compared to control. Antitumor activity against melanoma also manifested itself in the percentage of alive animals on the 31st day. In particular, the survival rate for mice injected with $^{6M}Zn_e(Asp)_2$ at day 5 after inoculation of tumor cells was 80%, while only 20% of animals survived in the control group.

Table 3 shows growth kinetics of B16 melanoma during $^{64}Zn_e(Asp)_2$ therapy in group 2 and individual regimens of drug administration Example 2. In Vivo Study Supporting the Efficacy of the Claimed Method Carried Out in Mouse Models (Intravenous/Intravenous+ Intratumoral Administration of $^{64}Zn_e(Asp)_2$)

An experimental model of hematogenous metastasis was used in the experiment which allowed for the inoculation of B16 melanoma cells. The characteristic of these cells is given in Example 1. The cells were cultured in vitro under standard conditions. For transplantation, tumor cells were removed from the substrate with 0.02% Versene solution and the suspension cellularity and viability were evaluated in the presence of trypan blue in a hemocytometer and the suspension was adjusted to a concentration of $1 \times 10^6$ cells/ml. Melanoma cells were injected intracutaneously (IC) in 0.05 ml of suspension ($0.5 \times 10^6$ cells/mouse) into the back area of the animal. Part of the coat on the back of mice was removed with a depilatory cream at 24 hours before tumor cell inoculation. Cells isolated from B16 mouse melanoma were used in the experiment. Cells were cultured in vitro under standard conditions. For inoculation, tumor cells were removed from the substrate with 0.02% Versene solution. The cellularity and viability of the obtained cell suspension were evaluated with a hemocytometer in presence of a trypan blue. Cell concentration was adjusted with saline to $1 \times 106$ cells/ml. Melanoma cells were injected IV in 0.2 ml of suspension ($0.2 \times 10^6$ cells/mouse) into the lateral tail vein.

$^{64}Zn_e(Asp)_2$ was dissolved in deuterium-depleted water. The composition was injected intravenously using a microinjection syringe at a dose of 60 μg of $^{64}Zn_e$/mouse: two injections at a dose of 30 μg/mouse, each in a volume of 0.3 ml (0.6 ml in total), for 4 hours. The injections were given every other day for 10 days (5 injections in total). The first injection of the inventive composition was given 45 minutes or 24 hours after inoculation of tumor cells. At day 26 after IV injection of tumor cells the lungs were excised from all animals in each group and the number and volume of metastases were then determined. $C_{57}B1$ mice (8 mice per group) at the age of 12-14 weeks, weighing 25-27 g were used in the experiment. The conditions in which animals were maintained are described in Example 1 above.

Before the experiment, all the animals were healthy, with normal behavioral performance. During the experiment, the animals were maintained in plastic cages under natural light illumination on a standard diet with free access to food and water.

The $^{64}Zn_e(Asp)_2$ composition was injected intravenously into the animal's lateral tail vein using a Micro-Fine Plus microinjection syringe (Becton Dickinson). The injection site was cleaned with 96% ethanol.

All the animals in cages were examined daily in order to determine mortality or any signs of deviations in their health status. A thorough examination was performed each time any abnormalities were detected. All deviations were recorded.

Statistical processing of the results was carried out using STATISTICA 6.0 software package designed for analysis in medical and biological statistics using the Student's t-test.

The animals were divided into experimental groups as follows:
  Group No. 1: control group, mice injected IV with B16 melanoma cells+IV injection of the solvent (deuterium-depleted water);
  Group No. 2: mice injected IV with B16 melanoma cells+IV injection of $^{64}Zn_e(Asp)_2$ 24 hours after the tumor cells were inoculated;
  Group No. 3: mice injected IV with B16 melanoma cells+IV injection of $^{64}Zn_e(Asp)_2$ 45 minutes after the tumor cells were inoculated The growth of metastases was assessed as follows.

On day 26 after IV injection of tumor cells the lungs were excised from all animals in each group and the number and volume of metastases were then determined.

The volume of metastases was calculated using the following formula for the volume of a sphere:

$V = 4/3 \times \pi r^3$, where V is the metastasis volume (mm$^3$); r is the metastasis radius (mm).

Figure 5A:
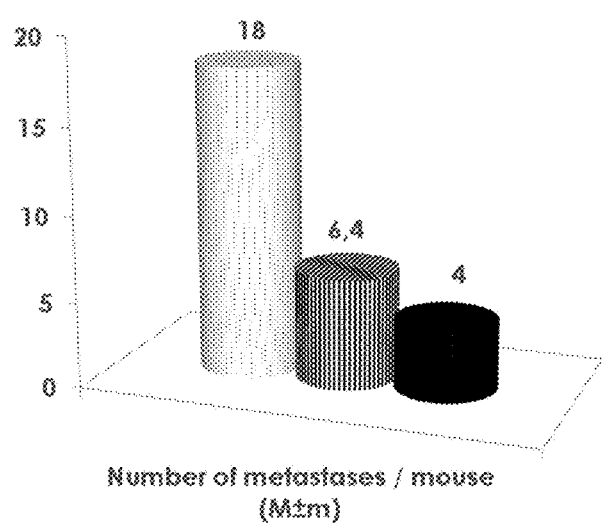
FIG. 5A—FIG. 5B show data on the quantitative evaluation of metastatic activity of melanoma cells after intravenous administration of $^{64}Zn_e(Asp)_2$ 45 minutes and 24 hours after transplantation of tumor cells, represented as the mean number of metastases (FIG. 5A) and the percentage of inhibitions of metastatic activity (FIG. 5B).
Figure 5B:
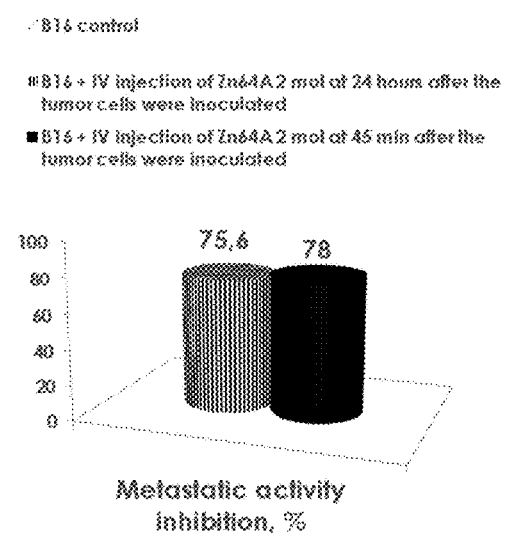

To assess the in vivo antimetastatic activity of $^{64}Zn_e(Asp)_2$ in the experimental model of hematogenous B16 melanoma metastasis, data on the number and volume of metastases in the lungs of mice were used. The results of the experiment are shown in Table 4 and in FIGS. 1, 2, 3, 4A, 4B, 4C, 5A and 5B.

TABLE 4

Characteristics of metastatic activity of B16 melanoma cells under the effect of $^{64}Zn_e(Asp)_2$

| Experimental group | Number of metastases/ mouse (M ± m) | Volume of metastases/ mouse, mm$^3$ (M ± m) | Number of animals in the group with metastases, % |
|---|---|---|---|
| B16 control | 18 ± 4.8 | 15.8 ± 5.4 | 100 |
| B16 + IV injection of $^{64}Zn_e(Asp)_2$ at a dose of 60 µg/mouse 24 hours after the tumor cells were inoculated | 6.4 ± 2.5 | 3.3 ± 2* | 75 |
| B16 + IV injection of $^{64}Zn_e(Asp)_2$ at a dose of 60 µg/mouse 45 min after the tumor cells were inoculated | 4 ± 2* | 2.5 ± 1.7* | 75 |

*p < 0.05 vs. control
M-the arithmetic mean, and m-standard error of the mean M (i.e., standard error of the M value)

M—the arithmetic mean, and m—standard error of the mean M (i.e., standard error of the M value)

The above results confirm the efficacy of $^{64}Zn_e(Asp)_2$ in suppressing the development of metastatic process of melanoma. A statistically significant decrease in the number and volume of metastases after the use of selected routes of administration was demonstrated. The effect was more pronounced, both in volume and in the number of metastatic lesions of the lung tissue, where the injection was given within a shorter time (45 min) after the tumor cells were inoculated, which indicates good prospects and the need to shorten the time between the onset of tumor growth, the spread of malignant cells and the beginning of therapy with $^{64}Zn_e(Asp)_2$.

A possibility of simultaneous intratumoral and intravenous administration of the composition comprising $^{64}Zn_e(Asp)_2$ was assessed in additional experiments (data not shown). These experiments confirmed the efficacy of $^{64}Zn_e(Asp)_2$ in suppressing the metastatic process in the body, which displayed itself in a decrease in tumor size, an increase in the number of surviving animals, and a decrease in the number of metastases.

Example 3. Study of the Distribution of Light and Heavy Isotopes of Chemical Elements in Samples of Cutaneous Melanoma The distribution of isotopes of various chemical elements in samples of cutaneous melanoma from experimental animals and corresponding samples taken from healthy animals was analyzed and compared in the experiment. Glow discharge mass-spectrometry was used for the determination of trace elements. The samples for the analysis were prepared as follows.

1. A sample of prepared tissue weighing up to 1 g was submerged in liquid nitrogen. With superfast cooling at a speed of about 1000 per 1 sec, most of the water turns into amorphous ice, the structure of which differs little from the structure of water and does not undergo volumetric expansion. Due to this fact, the structure of the tissue, after being frozen, does not change at the cellular level.

2. Amorphous ice was removed by sublimation under vacuum at a low temperature with automatic supply of dry nitrogen to the drying chamber to accelerate the sublimation process. The volume of gas supplied to the drying chamber did not exceed 0.1 l/min. The drying time of the sample under these conditions was about 10 hours.

3. Secondary drying was carried out under vacuum. To this end, at a stage of almost complete (up to 99%) dehydration, the sample was heated to a temperature of 35-40° C. under vacuum and isothermally held under these conditions for about 1 hour.

A constant mass of the sample until two identical mass values were obtained was a criterion for the completion of the drying process. During the last 3 hours of the drying process, the biomaterial sample was removed from the vacuum chamber every hour and weighed on an analytical balance. The drying process was stopped as soon as two identical values of the mass were obtained.

After completion of the sublimation process, the dry sample was removed from the vacuum chamber and laid in thin layers (not more than 5 m each layer) between copper grids fixed in the cage. 50 semi-circular copper grids 50-100 microns thick were used which were tightly pressed together by a metal clamp holding them. The "sandwich" prepared in this way for mass spectrometric analysis consisted of 50 copper grids, between which the test material was firmly pressed.

The analyzed area on the clamp surface was a circle 10 mm in diameter, in the center of which there were copper grids with the sample pressed in between them.

Finnigan ELEMENT GD glow discharge mass-spectrometer with the following specifications was used in the experiment:
  Dynamic range>$10^{12}$ linear with automatic cross calibration (from matrix elements (100%) to ultra-traces (ppt);
  Sensitivity (peak height, total ion current): >$1 \times 10^{10}$ cps, $1.6 \times 10^{-9}$ A;
  Dark Noise<0.2 cps
  Mass resolution>10000;
  Mass stability 25 ppm/8 hour Results of the study are shown in Table 5.

TABLE 5

Distribution of isotopes of chemical elements in samples of mouse cutaneous melanoma

| Element | Isotope | Value 1 | 2 | 3 | 4 | 5 | 6 | Mean value | Control (normal tissue) |
|---|---|---|---|---|---|---|---|---|---|
| Mg | Mg24 | 74.93 | 75.07 | 75.02 | 79.91 | 73.40 | 75.80 | 75.69 | 78.99 |
|  | Mg25 | 10.98 | 10.63 | 11.15 | 9.16 | 10.25 | 8.54 | 10.12 | 10.00 |
|  | Mg26 | 13.09 | 14.30 | 13.78 | 14.66 | 14.43 | 14.87 | 14.19 | 11.01 |
| Si | Si28 | 91.92 | 90.91 | 94.12 | 93.48 | 91.15 | 90.32 | 91.98 | 92.23 |
|  | Si29 | 5.56 | 6.06 | 3.53 | 3.62 | 5.51 | 6.45 | 5.12 | 4.67 |
|  | Si30 | 2.53 | 3.03 | 2.35 | 2.90 | 3.34 | 3.23 | 2.90 | 3.10 |
| Cl | Cl35 | 74.66 | 75.52 | 77.27 | 74.94 | 76.10 | 75.34 | 75.64 | 75.77 |
|  | Cl37 | 25.34 | 24.48 | 22.73 | 25.06 | 23.90 | 24.66 | 24.36 | 24.23 |
| Ca | Ca40 | 96.94 | 96.94 | 96.94 | 96.94 | 96.94 | 96.94 | 96.94 | 96.94 |
|  | Ca42 | 0.71 | 0.68 | 0.67 | 0.69 | 0.69 | 0.72 | 0.69 | 0.65 |
|  | Ca43 | 0.14 | 0.13 | 0.14 | 0.13 | 0.13 | 0.13 | 0.13 | 0.14 |
|  | Ca44 | 0.03 | 0.06 | 0.06 | 0.06 | 0.05 | 0.02 | 0.05 | 2.09 |
|  | Ca46 | 0.00 | 0.00 | 0.00 | 0.00 | 0.00 | 0.00 | 0.00 | 0.00 |
|  | Ca48 | 2.19 | 2.19 | 2.19 | 2.19 | 2.19 | 2.19 | 2.19 | 0.19 |
| Fe | Fe54 | 2.84 | 2.27 | 2.95 | 2.31 | 2.60 | 2.74 | 2.62 | 5.80 |
|  | Fe56 | 91.86 | 91.61 | 91.47 | 91.52 | 91.33 | 91.81 | 91.60 | 91.72 |
|  | Fe57 | 4.01 | 5.84 | 5.20 | 5.90 | 5.90 | 6.17 | 5.50 | 2.20 |
|  | Fe58 | 0.28 | 0.28 | 0.28 | 0.28 | 0.28 | 0.28 | 0.28 | 0.28 |
| Zn | Zn64 | 44.32 | 44.21 | 43.36 | 43.73 | 43.79 | 43.32 | 43.79 | 48.60 |
|  | Zn66 | 26.56 | 27.88 | 29.55 | 30.05 | 27.61 | 27.13 | 28.13 | 27.90 |
|  | Zn67 | 6.55 | 6.26 | 7.37 | 7.62 | 7.52 | 7.84 | 7.20 | 4.10 |
|  | Zn68 | 21.97 | 21.04 | 21.12 | 20.49 | 20.57 | 20.11 | 20.88 | 18.80 |
|  | Zn70 | 0.60 | 0.60 | 0.60 | 0.60 | 0.60 | 0.60 | 0.60 | 0.60 |
| Rb | Rb85 | 55.00 | 47.22 | 42.42 | 34.48 | 33.33 | 35.14 | 41.27 | 72.16 |
|  | Rb87 | 45.00 | 52.78 | 57.58 | 65.52 | 66.67 | 64.86 | 58.73 | 27.84 |

As can be seen from the table above, the results confirm our hypothesis that pathological changes due to chirality can be induced by isotopic substitutions. Thus the administration of $^{64}Zn_e(Asp)_2$ according to the present invention can prevent and restore the normal isotope distribution necessary for the successful functioning of proteins, such as a transcription factor or a protein that controls the cell cycle, and thereby suppress formation of malignant tumors.

Example 4

For the experiment, $^{64}Zn_e(Asp)_2$ was synthesized from $^{64}Zn_e$ oxide and was in a powdered form after the synthesis. A solution of the concentration required for the experiment was prepared immediately prior to its administration to the animals by dissolving the required amount of obtained $^{64}Zn_e(Asp)_2$ powder in physiological saline or in deuterium-depleted water.

The method of atomic emission spectroscopy with an inductively coupled plasma was endured to confirm the presence of Zinc cation in the sample. Prior to determination the sample was treated with a mixture of mineral acids in a Teflon autoclave under the action of microwave radiation. The presence of Zinc in the sample was confirmed as the main cation; its approximate content was 17,6%, The impurities of other element s was also revealed.

Determination of Zn content also was made with complexometric titration method with eriochrome black T as an end-point indicator, It was found that content of zinc in the sample to be 17.98±0.17%.

The confirmation the presence of aspartate ion and determination of its optical isomer form was carried out by liquid chromatography with detection at 254 nm wavelength using chiral chromatography column Chiralcel OD-R. Previously, derivatization was carried out usmg isophenyl cyanate. Also the chromatograms of derivatized standards of the racemic mixture D. L-aspartic acid and pure L-aspartic acid were obtained. It was shown that sample contains L-isomer only.

A zinc content was found to be 17,98±0,17% corresponding to 90,8-0,9% of Zinc L-aspartate.

Determination of the relative content of $^{64}Zn$ in the sample was performed after dissolution of sample pail in deionized water and dilution to a concentration of 1.33 ppm based on zinc. Ratio of signal intensities of $^{64}Zn$, $^{66}Zn$, $^{67}Zn$, $^{68}Zn$, and $^{70}Zn$ isotopes were measured for sample solution with Agilent 7500ce inductively coupled plasma mass-spectrometer. The results are shown in Table 6. The sample was enriched for $^{64}Zn$, measured at 99.39%.

TABLE 6

| Isotope | Signal intensity, cps | Rational content % | Isotope distribution in nature, rational content % * |
|---|---|---|---|
| $^{64}Zn$ | 17 811 884.90 | 99.39 | 49.17 |
| $^{66}Zn$ | 70 776.20 | 0.3949 | 27.73 |
| $^{67}Zn$ | 8 779.26 | 0.0490 | 4.04 |
| $^{68}Zn$ | 27 976.10 | 0.1561 | 18.45 |
| $^{70}Zn$ | 1 184.63 | 0.0066 | 0.61 |

Sulfate ion content in the sample solution was determined by turbidimetry method using Barium chloride. The content of sulfates in the sample was found to be 0,66±0.032%.

Elemental impurities and impurities of sulfate ion in the sample were determined. Elemental impurities were recovered by atomic emission spectroscopy with an inductively coupled plasma. Prior to determination, the sample was treated with a mixture of mineral acids in a Teflon autoclave under the action of microwave radiation. Impurities of Phosphorus, Calcium, Sodium, Silver, Aluminum, Bismuth, Copper, Ferum, Potassium, Magnesium and Plumbum were detected, as shown in Table 7.

TABLE 7

| Impurity | Content, % | Impurity | Content, % |
|---|---|---|---|
| P | 0.1 | Fe | 0.01 |
| Ca | 0.08 | Ag | 0.01 |
| Na | 0.05 | Al | 0.01 |
| Bi | 0.01 | K | 0.01 |
| Cu | 0.01 | Mg | 0.01 |
|  |  | Pb | 0.0054 |

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

What is claimed is:

1. A method of reducing melanoma tumor growth of a primary melanoma in a patient in need thereof, comprising suppressing tumor growth of the primary melanoma by administering a composition comprising a therapeutically effective amount of $^{64}Zn_e(Asp)_2$ to said patient wherein from 0.2 ug/kg to 2000 mg/kg patient weight/day of $^{64}Zn_e(Asp)_2$ is administered to the patient and; wherein the $^{64}Zn_e(Asp)_2$ is at least 90% $^{64}Zn$ and is administered intratumorally to the primary melanoma of said patient.

2. The method of claim 1, wherein the composition is an aqueous solution.

3. The method of claim 1, wherein the composition is administered once a day.

4. The method of claim 1, wherein the composition is administered more than once a day.

5. The method of claim 1, wherein the composition further comprises deuterium-depleted water as a solvent.

* * * * *